(12) United States Patent  
Schmidt

(10) Patent No.: US 8,087,702 B2  
(45) Date of Patent: Jan. 3, 2012

(54) CONNECTOR FOR A DIALYSIS PORT

(75) Inventor: Helmut Schmidt, Oberthal (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 12/801,956

(22) Filed: Jul. 2, 2010

(65) Prior Publication Data  
US 2011/0084479 A1 Apr. 14, 2011

Related U.S. Application Data

(63) Continuation of application No. 12/385,415, filed on Apr. 7, 2009, now abandoned.

(30) Foreign Application Priority Data

Nov. 10, 2003 (DE) .................................. 103 52 859

(51) Int. Cl.  
F16L 37/00 (2006.01)

(52) U.S. Cl. ................... 285/305; 285/326; 210/321.71; 210/321.78

(58) Field of Classification Search .................. 285/326, 285/305, 308; 210/232, 195.2, 321.71, 321.78, 210/321.79  
See application file for complete search history.

(56) References Cited

U.S. PATENT DOCUMENTS

| 2,092,243 | A | * | 9/1937 | Breese | 285/305 |
| 4,198,080 | A | * | 4/1980 | Carpenter | 285/316 |
| 4,331,540 | A | * | 5/1982 | Witsoe | 210/321.78 |
| 4,496,458 | A | * | 1/1985 | Lee | 210/321.65 |
| 5,040,831 | A | * | 8/1991 | Lewis | 285/305 |
| 5,052,725 | A | * | 10/1991 | Meyer et al. | 285/308 |
| 5,158,569 | A | * | 10/1992 | Strickland et al. | 604/533 |
| 5,165,728 | A | * | 11/1992 | Mayer | 285/316 |
| 5,813,703 | A | * | 9/1998 | Reinholz | 285/305 |
| 5,997,048 | A | * | 12/1999 | Hulzebos | 285/305 |
| 6,132,402 | A | * | 10/2000 | Tessmann et al. | 285/305 |
| 7,017,948 | B2 | * | 3/2006 | Sunohara et al. | 285/239 |
| 7,270,350 | B2 | * | 9/2007 | Cronley | 285/326 |
| 2005/0006297 | A1 | * | 1/2005 | Moriwaki et al. | 210/321.6 |

* cited by examiner

Primary Examiner — David E Bochna  
(74) Attorney, Agent, or Firm — Jacobson Holman PLLC

(57) ABSTRACT

A connector for connecting a dialysate port of a dialyzer with a dialysate-carrying line and a dialyzer. The connector has a recess with a shift element on the end which accommodates the dialyzer port. The shift element is accommodated in the recess and is displaceable between a first position and a second position perpendicular to the direction of the lumen on the first end. The shift element does not pass through the lumen in the first position. In the second position, the lumen is constricted so that the connector with the shift element can be placed on the dialysate port and the connector locked on the dialysate port through engagement of the shift element behind an undercut on the port.

16 Claims, 3 Drawing Sheets

CONNECTOR FOR A DIALYSIS PORT

RELATED APPLICATIONS

This application is a continuation application of application U.S. Ser. No. 12/385,415 filed Apr. 7, 2009, now abandoned, which is a continuation application of application U.S. Ser. No. 10/578,743 filed May 10, 2006, now abandoned, which is a 371 of PCT application No. PCT/EP04/011947 filed Oct. 22, 2004, and hereby claims the priorities thereof to which it is entitled.

BACKGROUND OF THE INVENTION

1. Field of the Invention

The present invention relates to a connector for connecting a dialysate port of a dialyzer to a dialysate-carrying line with a first lumen and a second lumen passing through the connector, a first end of the connector surrounding the first lumen, suitable for accommodating the dialysate port in the first lumen, a second end of the connector surrounding the second lumen and suitable for being connected to the dialysate-carrying line.

2. Description of Related Art

During a hemodialysis treatment, blood is taken from a patient with the help of an extracorporeal circulation and is passed through a dialyzer. Such dialyzers today consist of a bundle of thousands of semipermeable hollow fiber membranes through the interior of which the blood is passed. A cleaning fluid—the dialysis fluid or the dialysate—is circulated on the outside of the hollow fibers so that the substances to be removed from the blood enter this fluid by diffusion and/or convection.

Such a dialyzer generally has four liquid connections, which are known as ports: two for blood and two for the dialysate. The tubing system of the extracorporeal blood circulation and the dialysate-carrying line system in the sense of one incoming line and one-outgoing line is connected to these ports. For the purpose of uniformity in use, standardized port forms are used for the blood ports on the one hand and for the dialysate ports on the other hand. Although the connecting system for the blood tubing system is designed to work with disposable items, the tubing used for the lines carrying the dialysate with many dialyzers for treatment of chronic renal insufficiency is reusable. The Hansen coupling, as it is called, is used as the connecting system. With the Hansen coupling, the connection to the dialysate port is locked by a metallic ball bearing element. According to DIN 58352, a German standard, the dialysate port consists of an essentially tubular projection having a peripheral undercut upstream from the end of the port in the sense of a reduced outside diameter in which the balls of the ball bearing element engage. Between individual treatments, the dialysate-carrying lines are rinsed and cleaned together with the remaining dialysate circulation.

However, with other dialyzers, disposable tube sets are also used for the dialysate-carrying lines. In this case it is expedient to use a design different from the Hansen coupling for the corresponding connector, in particular when the connector is also a disposable part.

EP 0 442 310 A1 describes dialyzer ports of a dialyzer which allow connection of Hansen couplings as well as other connectors. To this end, the dialyzer port is provided with a thread onto which a corresponding connector mating piece can be screwed.

A screwing motion to establish the connection is a disadvantage inasmuch as it is difficult to determine the endpoint of the screwing motion. Leakage may occur if the connector is not screwed on adequately, while on the other hand, if too much force is applied to the end of the connector, it may quickly result in damage to the sealing elements, which are generally provided in these connectors. In addition, this connector may be used only when the ports on the dialyzers are also designed accordingly, i.e., design measures are also required on the mating piece of the connector.

SUMMARY OF THE INVENTION

The object of the present invention is to improve upon a generic connector, so that it can be manufactured suitably as a disposable item while at the same time permitting simple and reliable connection of a dialysate-carrying line to a dialysate port of a dialyzer without requiring structural measures on the dialyzer itself.

According to the teaching of this invention, this object is achieved by a connector for connecting a dialysate port of a dialyzer having a dialysate-carrying line with a first lumen and a second lumen passing through the connector, the first end of the connector surrounding the first lumen and suitable for accommodating the dialysate port in the first lumen. The second end of the connector, surround the second lumen and is suitable for being connected to the dialysate-carrying line. A recess with a shift element accommodated therein is provided on the first end, whereby the shift element is displaceable between a first position and a second position perpendicular to the direction of the first lumen in the first end of the connector. In the first position, the shift element does not penetrate through the first lumen and, in the second position, the shift element narrows the first lumen so that the connector with the shift element is placed on the dialysate port in the first position and in the second position it can be locked on the dialysate port by means of an undercut thereon.

According to one design embodiment, the connector includes not only the shift element but also a base body which is composed of two interconnected essentially cylindrical sleeves whereby the first sleeve is the first end and the second sleeve is the second end. Preferably, the outside diameter of the first sleeve is greater than the outside diameter of the second sleeve, and the first sleeve is suitable for accommodating a port according to DIN 58352.

Further, the first lumen in the first sleeve can have a larger diameter than the second lumen in the second sleeve. The connector can also be provided with a stop for the dialyzer port in the connecting area of the two sleeves. In addition a sealing element may be provided on the inside wall of the first sleeve near the stop for sealing the connector with respect to the dialyzer port.

According to another embodiment, the connector includes a constriction area in the first and second lumens between the first and second ends of the connector.

In addition, the recess may include two opposite recesses. In this case, the shift element has a first opening which does not constrict the first lumen in the first position and has a second opening which is connected to the first opening in the direction of shifting and which constricts the first lumen in the direction of the opposite recesses in the second position. The first opening can have a round shape and the second opening can have an elongated shape so that the overall shape is that of a keyhole. Further, the first opening can have catch projections which can engage with complementary recesses on the first end of the connector for the purpose of engaging the shift element in the first position. These complementary recesses may be additionally provided symmetrically on the first end of the connector on the opposite side of the first lumen in the direction of shifting.

According to a further embodiment, the second opening is provided with an expanded opening area perpendicular to the direction of shifting for accommodating the dialyzer port for engagement of the shift element in the second position. The elongated border of the second opening can have a wall thickness that tapers with a slope toward the opening and can have a form-fitting engagement with a corresponding slope on the undercut of the dialyzer port.

This invention is based on the observation that the dialysate port designed according to German standard DIN 58352 has a peripheral undercut on the outside. This undercut can be used for a shift element that is provided on the connector designed according to this invention for locking the connector. In this case it is not necessary to redesign the port on the dialyzer end.

BRIEF DESCRIPTION OF THE DRAWINGS

Additional details and advantages of this invention are described in greater detail below on the basis of an exemplary embodiment as depicted in the drawings.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
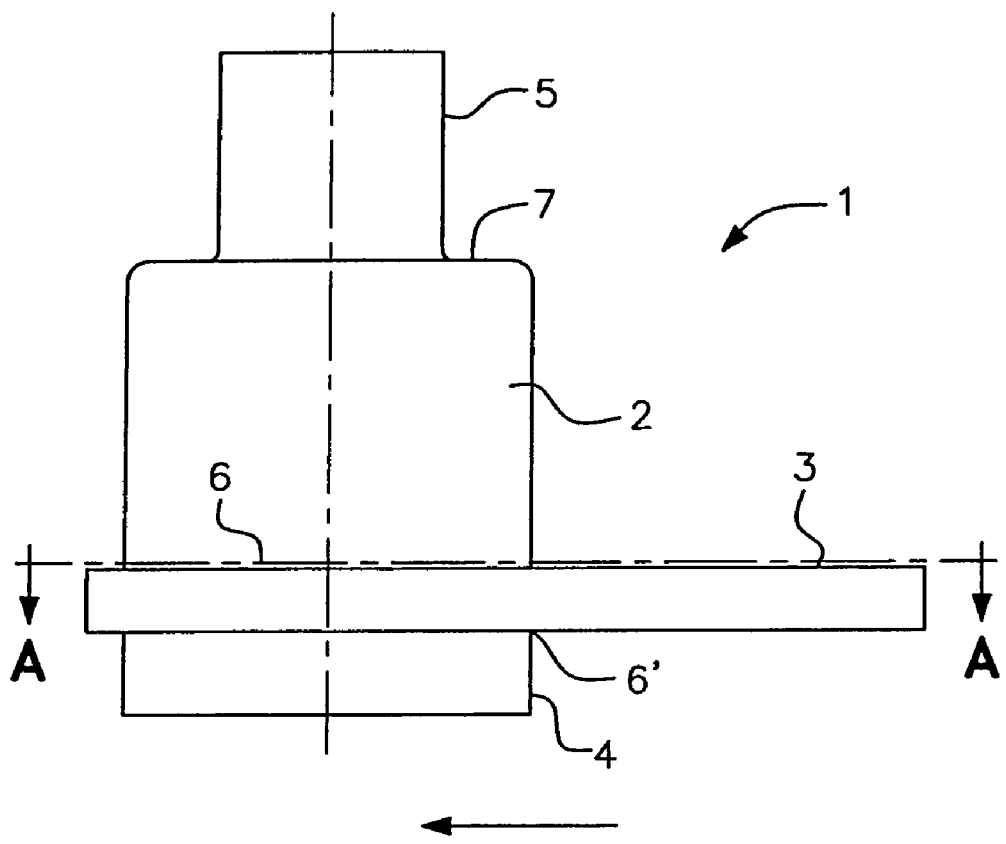
FIG. 1 is a side view of an embodiment of the inventive connector with the shift element in the first position.
Figure 3A:
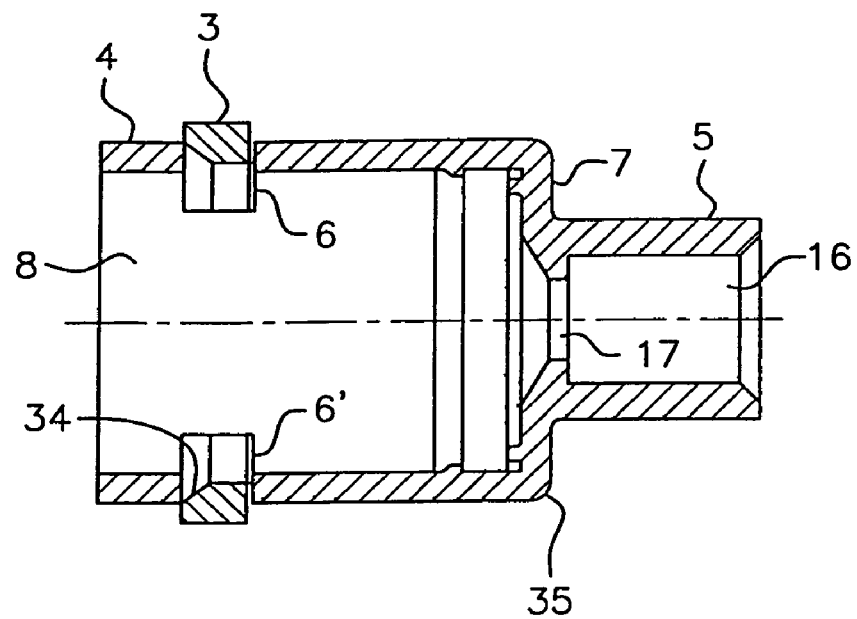
FIG. 3a is a section through the connector from FIG. 1 along the axis of symmetry and as seen in the direction of shifting of the shift element, whereby the shift element is in the first position.
Figure 3B:
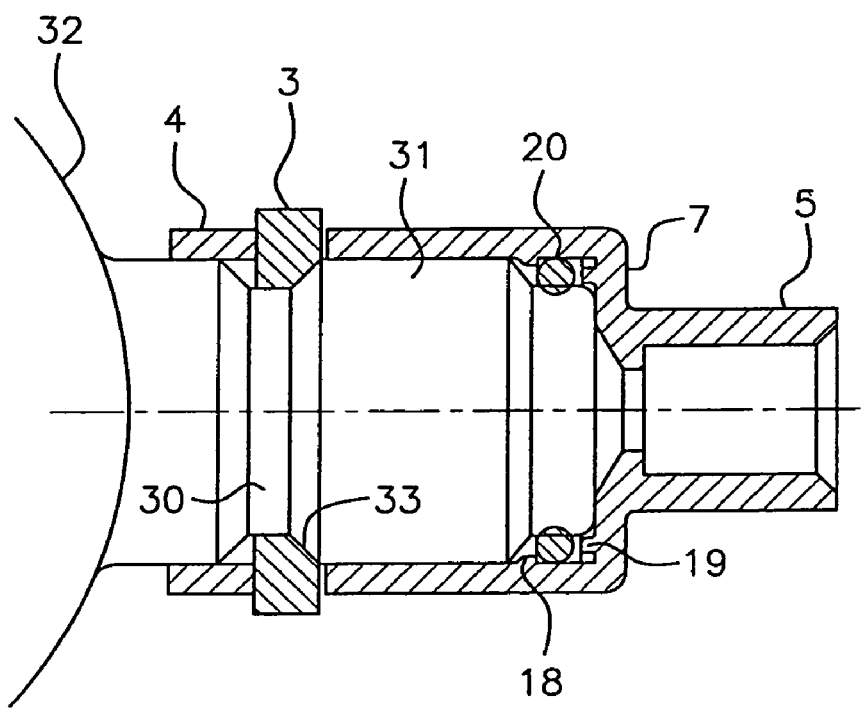
FIG. 3b shows a view corresponding to that in FIG. 3a, showing the shift element in the second position.

FIG. 1 shows an embodiment of the inventive connector 1 for connecting a dialysate port of a dialyzer to a dialysate-carrying line (not shown) in a side view. The connector 1 consists of a base body 2 and a shift element 3. The base body 2 is composed of a first cylindrical sleeve 4, which is situated on the first end of the connector 1 that is to be connected to the dialyzer port, and a second cylindrical sleeve 5, which is situated on the second end of the connector 1 that is to be connected to the dialysate-carrying line. The outside diameter of the first sleeve is greater than the outside diameter of the second sleeve, which is determined by the dimensions of the lines to be connected. The two sleeves have a fluid-tight connection in a connecting area 7, as shown in FIGS. 3a and 3b. A lumen (not shown in FIG. 1) extends through the base body of the connector, and in the case of the connection, some of the dialysate flows through this lumen, and for the remainder, it accommodates the dialysate port of the dialyzer.

A recess 6 is provided on the side facing the view in FIG. 1, and a recess 6' is provided on the opposite side (not shown) to accommodate the shift element 3 in the first end 4 of the connector 1. The shift element 3 is shown in the first position in FIG. 1. It can be moved into the second position in the direction of the arrow.

Figure 2A:
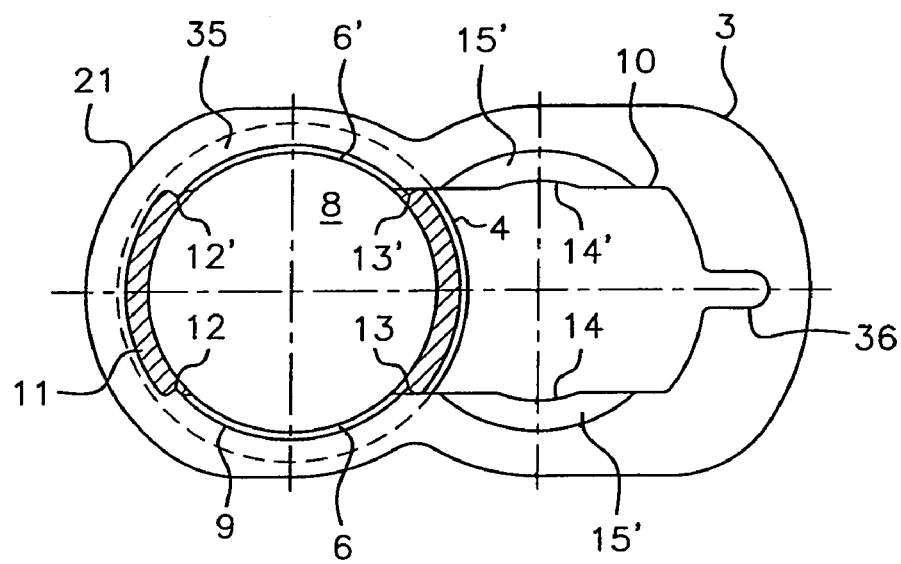
FIG. 2a is a view of Section A-A in FIG. 1.

FIG. 2a shows a section view A-A from the view in FIG. 1. The shift element 3 is in the first position accordingly. This shows the lumen 8 of the first cylindrical sleeve 4 and the recesses 6 and 6' in which the shift element 3 can be moved from the first position into the second position.

The shift element 3 also has an overall keyhole-shaped opening composed of a first round opening 9 and a second elongated opening 10 connected to the firmer in the shift direction. In the first position of the shift element 3 shown in FIG. 2a, the first opening 9 is arranged concentrically with the lumen 8 of the first end 4 of the connector 1 so that the lumen 8 is not constricted. The first opening 9 is widened slightly in an area 11 opposite the second opening 10, so that projections 12 and 12' that point inward are formed at the border with the expanded opening 11. Recesses that are complementary to these projections are formed in the recesses 6 and 6', so that the projections 12 and 12' can engage in them. These recesses are also provided symmetrically on the opposite side of the first sleeve 4 where they are labeled as 13 and 13'. This had the advantage that the base body 2 has mirror symmetry with respect to the plan perpendicular to the shift direction, which makes complex orientation of the base body 2 in assembly with the shift element 3 superfluous.

Due to the enlargement of the projections 12 and 12', the connector 1 can be supplied with the shift element 3 in the first position without the user having to convince himself by actuation of the shift element 3 that the first opening 9 is aligned with the lumen 8 when the connector is used. The bracket 21 on the shift element 3 then comes to a stop on the base body 2 on the outside of the base body.

Figure 2B:
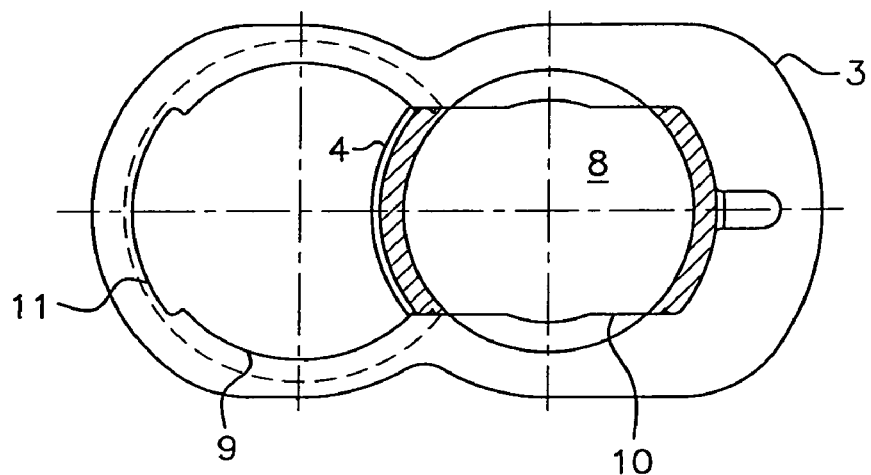
FIG. 2b is a view corresponding to that in FIG. 2A, showing the shift element in the second position.

An enlarged opening area 14 and 14' is provided in the second opening 10, running concentric with the lumen 8 when the shift element is in the second position (FIG. 2b). In this position the second opening 10 constricts the lumen 8 in the direction of the recesses 6 and 6'. The contours of the opening areas 14 and 14' conform to those of the dialysate port of the dialyzer. Due to the slightly restricted width of the opening 10 directly next to the, regions 14 and 14' the shift element 3 is also held in the second position—with the dialysate port inserted (not shown in FIG. 2b).

The spring force to be overcome can be adjusted through the desired dimensioning of a constriction 36. Since both the base body 2 and the shift element 3 are also preferably both made of plastic, the projections 12 and 12' as well as the opening areas 14 and 14' can be dimensioned easily and thus a material can be selected so that the catch operations can be performed without exerting excess force while nevertheless achieving a reliable locking which is discernible, in particular audible.

Regions 15 and 15' in which the wall thickness of the shift element 3 is reduced in the sense of a slope toward the opening 10 are connected to the opening areas 14 and 14'. The function of this slope will be explained later on the basis of FIG. 3b.

FIG. 3a shows a section along the axis of symmetry of the connector 1 in the direction of displacement of the shift element 3, whereby the shift element 3 is in the first position. In this view, the first sleeve 4 as well as the second sleeve 5 of the base body 2 can also be seen. The first sleeve 4 has a lumen 8 passing through it, and the second sleeve 5 has a lumen with a smaller diameter passing through it. There is a constriction 17 between the two lumens. The one-piece base body is connected by a ring-like wall 7 in the connecting area between the first and second sleeves. The recesses 6 and 6' to accommodate the shift element 3 are discernible at the first end 4 of the base body 2. Since the shift element 3 is in the first position, the lumen 8 is not impaired in being opened by the shift element.

The shift element 3 is designed to be flexible enough to easily be installed in this position on the base body 2 by spreading the leg-like borders of the first opening 9. This is facilitated by a peripheral slope 34, which is also shown with dotted lines in FIG. 2a and FIG. 2b. In assembly of the shift element 3 on the base body 2 from the side of the second sleeve 5, the shift element 3 is pressed with the round opening 9 onto the base body 21 so that the sloping surface 34 strikes the rounded borders 35 of the base body 2 in the connecting area 7. This facilitates forward shifting of the shift element 3 until it engages in the recesses 6 and 6'. As an alternative, the slope 34 may also be provided on the other side of the shift element 3 when assembly is to take place from the side of the first sleeve 4.

With the shift element 3 in the first position, the inventive connector can be pushed onto to the dialysate port. The connector 1 is then locked by shifting the shift element 3 into the second position (FIG. 3b). The shift element 3 then engages behind the undercut 30, which is designed as a peripheral groove and is provided in the dialysate port 31. The dialysate port 31 is part of a dialyzer housing 32.

The groove 30 is provided with a slope 33 inclined toward the end of the port. The regions 15 and 15' are designed to be form-fitting with this slope 33. This yields an axial force input which contributes toward securing the connector 1 on the port 31. The dialysate port 31 is pressed against the end face 7 of the base body 2, which at the same time serves as a stop for the port. In addition, peripheral projections 18 and 19, which serve to secure a sealing element 20 which may be designed as an O-ring, may be provided on the inside of the lumen 8. This gasket element 20 encloses the outer end of the port 31, which has a suitably reduced outside diameter at this point to achieve a reliable seal of the connector 1 with respect to the port 31.

In the simplest case, the dialysate-carrying line—e.g., in the form of a length of tubing—may be placed on the second sleeve 5. Depending on the requirement, fixation with a wing nut may also be provided. Other connecting methods or non-releasable connections which are preassembled, e.g., by gluing or welding, may also be used. Those skilled in the art will be familiar with a wide variety of skillful embodiments.

The inventive connector permits a connection of a dialysate-carrying line to a conventional port of a dialyzer which is easy and reliable to handle. Only a few individual parts are required, and those may be manufactured inexpensively from plastics by the injection molding technique. The connector may also be used with other ports whose connections can be inserted into the first end of the connector and which have an undercut that can be gripped with the help of the shift element for the purpose of locking. This is true in particular of all ports according to DIN 58352.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A dialyzer in combination with a connecting device comprising:
    a dialyzer having a dialysate port; and
    a connector configured to connect said dialysate port of said dialyzer to a dialysate-carrying line, said connector having a first lumen and a second lumen passing therethrough, a first end of the connector surrounding the first lumen and configured to accommodate the dialysate port in the first lumen, a second end of the connector surrounding the second lumen and configured for being connected to the dialysate-carrying line, said connector first end having two opposite recesses with a shift element accommodated in said recesses such that the shift element is displaceable between a first position and a second position perpendicular to the direction of the first lumen in the connector first end, said shift element having a first opening which does not constrict the first lumen in the first position and a second opening which is connected to the first opening in the direction of shifting and which constricts the first lumen in the direction of the opposite recesses in the second position, the first opening having a round shape and the second opening having an elongated border so that an overall shape of said first and second openings together is that of a keyhole, said shift element in the second position narrowing the first lumen so that the connector with the shift element is placed on the dialysate port in the first position and, when the shift element is moved into the second position, the connector is locked on the dialysate port through engagement of the shift element behind an undercut on said port, said undercut having a slope inclined toward a connection end of said port, the elongated border of the second opening having a wall thickness that tapers with a corresponding slope toward the opening to have a form-fitting engagement with the slope on the undercut of said dialyzer port when the connector is secured to the port.

2. The combination according to claim 1, wherein the connector further includes a base body which is composed of two interconnected essentially cylindrical sleeves, the first sleeve being the first end and the second sleeve being the second end.

3. The combination according to claim 2, wherein an outside diameter of the first sleeve is greater than an outside diameter of the second sleeve.

4. The combination according to claim 2, wherein the first lumen in the first sleeve has a larger diameter than the second lumen in the second sleeve.

5. The combination according to claim 2, wherein the connector is provided with a stop for the dialyzer port in the connecting area of the two sleeves.

6. The combination according to claim 5, wherein a sealing element for sealing the connector with respect to the dialyzer port is provided on the inside wall of the first sleeve near the stop.

7. The combination according to claim 1, wherein a constriction area in at least one of the lumens is provided between the first end and the second end.

8. The combination according to claim 1, wherein the first opening has catch projections configured to engage with complementary recesses formed in said opposite recesses on the first end of the connector for engaging the shift element in the first position.

9. The combination according to claim 8, wherein the complementary recesses are additionally provided symmetrically on the first end of the connector on the opposite side of the first lumen in the direction of shifting.

10. The combination according to claim 1, wherein the second opening is provided with an expanded opening area perpendicular to the direction of shifting for accommodating the dialyzer port for engagement of the shift element in the second position.

11. The combination according to claim 1, wherein said dialysate port is configured to be coupled to a Hansen coupling and wherein said dialysate port when receiving said connector remains in said same configuration as when said port is coupled to a Hansen coupling.

12. The combination according to claim 11, wherein the connector further includes a base body which is composed of two interconnected essentially cylindrical sleeves, the first sleeve being the first end and the second sleeve being the second end.

13. The combination according to claim 12, wherein an outside diameter of the first sleeve is greater than an outside diameter of the second sleeve.

14. The combination according to claim 12, wherein the first lumen in the first sleeve has a larger diameter than the second lumen in the second sleeve.

15. The combination according to claim 12, wherein the connector is provided with a stop for the dialyzer port in the connecting area of the two sleeves.

16. The combination according to claim 15, wherein a sealing element for sealing the connector with respect to the dialyzer port is provided on the inside wall of the first sleeve near the stop.

* * * * *